United States Patent
Bian et al.

(12)

(10) Patent No.: US 11,596,378 B2
(45) Date of Patent: Mar. 7, 2023

(54) DEVICE AND METHOD FOR DETECTING PHYSIOLOGICAL SOUND

(71) Applicant: SHANGZHI MEDICAL TECHOLOGY (HANGZHOU) CO., LTD., Hangzhou (CN)

(72) Inventors: Junjie Bian, Hangzhou (CN); Wenchu Zou, Hangzhou (CN); Xuhui Zou, Hangzhou (CN)

(73) Assignee: SHANGZHI MEDICAL TECHOLOGY (HANGZHOU) CO., LTD., Hangzhou (CN)

( * ) Notice: Subject to any disclaimer, the term of this patent is extended or adjusted under 35 U.S.C. 154(b) by 322 days.

(21) Appl. No.: 16/649,568

(22) PCT Filed: Oct. 22, 2018

(86) PCT No.: PCT/CN2018/111226
§ 371 (c)(1),
(2) Date: Mar. 20, 2020

(87) PCT Pub. No.: WO2019/076383
PCT Pub. Date: Apr. 25, 2019

(65) Prior Publication Data
US 2020/0281558 A1 Sep. 10, 2020

(30) Foreign Application Priority Data

Oct. 22, 2017 (CN) .......................... 201710989100.5
Oct. 22, 2017 (CN) .......................... 201710989110.9
(Continued)

(51) Int. Cl.
*A61B 7/04* (2006.01)
*H04R 1/46* (2006.01)

(52) U.S. Cl.
CPC .................. *A61B 7/04* (2013.01); *H04R 1/46* (2013.01)

(58) Field of Classification Search
CPC .................................... A61B 7/04; H04R 1/46
See application file for complete search history.

(56) References Cited

U.S. PATENT DOCUMENTS 1,015,163 A * 1/1912 Fosgate .................... A61B 7/02
181/131
4,270,627 A * 6/1981 Hill .......................... A61B 7/02
181/131

FOREIGN PATENT DOCUMENTS

CN         1463675 A      12/2003
CN       107789005 A       3/2018
(Continued)

OTHER PUBLICATIONS

PCT/CN2018/111226 English Translation of the International Search Report and Written Opinion dated Jan. 4, 2019, 11 pp.

*Primary Examiner* — Andrew L Sniezek
(74) *Attorney, Agent, or Firm* — NZ Carr Law Office

(57) ABSTRACT

The invention relates to a device for detecting physiological sounds, the device comprising a thin film, and a first conductive element for conducting sounds, the conductive element being located on the thin film. In some embodiments, the detection device comprises a cavity; the thin film is a part of the cavity. The volume of the cavity is variable; the volume of the cavity is reduced, either when the conductive element contacts the skin of a human or a mammal, or before the conductive element contacts the skin of a human or a mammal, or after the conductive element contacts the skin of a human or a mammal. The device of the inventions can significantly improve the detection sensitivity and resolution of physiological sounds, and can give early diagnosis pathological sounds, for example, heart failure can be detected by heart sound diagnosis.

20 Claims, 9 Drawing Sheets

(30) Foreign Application Priority Data

| | | |
|---|---|---|
| Oct. 22, 2017 | (CN) | 201710989111.3 |
| Oct. 22, 2017 | (CN) | 201710989117.0 |
| Oct. 22, 2017 | (CN) | 201710989118.5 |
| Oct. 22, 2017 | (CN) | 201721361278.7 |
| Oct. 22, 2017 | (CN) | 201721361279.1 |
| Oct. 22, 2017 | (CN) | 201721361292.7 |
| Oct. 22, 2017 | (CN) | 201721361294.6 |
| Oct. 22, 2017 | (CN) | 201721361298.4 |
| Oct. 22, 2017 | (CN) | 201721361304.6 |
| Oct. 22, 2017 | (CN) | 201721361305.0 |
| Oct. 22, 2017 | (CN) | 201721361311.6 |
| Oct. 22, 2017 | (CN) | 201721395601.2 |

(56) References Cited

FOREIGN PATENT DOCUMENTS

| | | | |
|---|---|---|---|
| CN | 107811648 | A | 3/2018 |
| CN | 108354624 | A | 8/2018 |
| CN | 108354625 | A | 8/2018 |
| CN | 108366318 | A | 8/2018 |
| JP | 2014090916 | A | 5/2014 |

\* cited by examiner

DEVICE AND METHOD FOR DETECTING PHYSIOLOGICAL SOUND

CROSS REFERENCE TO RELATED APPLICATION

This application is a 35 U.S.C. § 371 national phase application of PCT/CN2018/111226, filed Oct. 22, 2018. PCT/CN2018/111226 claims the priority from Chinese Patent Application No. 201721361279.1, 201710989110.9, 201721361294.6, 201721361292.7, 201721361304.6, 201710989118.5, 201721361278.7, 201710989117.0, 201721361311.6, 201721361305.0, 201710989100.5, 201721361298.4, 201710989111.3 and 201721395601.2 filed on Oct. 22, 2017. The above patent applications are hereby incorporated by reference in their entirety.

TECHNICAL FIELD

The invention relates to the field of physiological information monitoring, in particular to a new device and method for detecting physiological sounds.

BACKGROUND ART

This is only an introduction to the background of the invention and cannot be considered as the prior art of the invention.

In the field of medical health, deaths resulting from heart problems account for a very high proportion of total deaths, and the diseases related to heart are characterized in sudden and high risk. Rome wasn't built in a day. Facing heart-related diseases, we not only need to mend, but also to improve health awareness and take preventive measures. Hence, it is of great significance for the prevention of heart-related diseases (such as high incidence of cardiovascular diseases) to monitor in real-time the ECG and heart sound of patients regularly, or to monitor the ECG and heart sound of non-patients on a regular or irregular basis for preventing heart damage.

Heart is the pump of a human body engine. Heart generates electrical simulation before mechanical contraction, produces a physical current which conducts onto the surface of a human body via tissue fluid and body fluid, so that different heart beat sounds are resulted in different parts to form a potential difference of different body surfaces. The heart problems can be prevented and monitored by means of recording and distinguishing the said real-time changes.

To ensure accurate heart status monitoring of medical or scientific research significance, a ECG and heart sound measuring instrument is required. Although some small devices have been used for detecting heart sounds, which detects sounds and converts them into electronic signal for output, to achieve automatic detection of heart sounds, however, as the generation of heart or other physiological sounds involves very complicated processes and conditions, some pathological sounds are very difficult to distinguish from each other, it is necessary to carry out early detection, distinguish pathological sounds, and provide early treatment.

SUMMARY OF THE INVENTION

The invention overcomes the shortage of the prior art, and provides a new device and method for detecting physiological sounds which is characterized in simple and rational structure, low cost and high use value.

On the one hand, the inventions provide a device for detecting sound, the device comprising a thin film, and an element for collecting or conducting sounds, the element being located on the thin film.

In some embodiments, the detection device comprises a closed cavity, and the thin film is a part of the cavity. In some embodiments, the conductive element is located on the thin film, outside the cavity.

In some other embodiments, before and during detecting physiological sounds, the cavity including the thin film is sealed and includes gas inside. In some embodiments, the cavity communicates with the outside atmosphere before detecting physiological sounds, and the cavity is in sealed state when the conductive element contacts the skin. In some embodiments, the cavity is communicated with the outside atmosphere through the conductive element, and the skin seals the conductive element to make the cavity in sealed state when the conductive element contacts the skin of a mammal or a human.

In some preferred embodiments, the sound conductive element is a metallic or nonmetallic element. The said sound conductive element can also be called a "concentrator head". In some embodiments, the area that the conductive element contacts the surface of a mammal is smaller than the area of the thin film. In some embodiments, the metal is of conductive metal, such as iron, copper, aluminum, gold, silver, or any other metallic conductor or alloy. Certainly, it can also be other nonmetallic conductors, such as carbon rod. In some embodiments, the density of the thin film is smaller than the density of the conductive element, or the weight per unit volume of the conductive element is smaller than the weight per unit volume of the thin film.

In some embodiments, the volume of the closed space is changed when the conductive element contacts or before, during or after the conductive element detects physiological sounds. In some embodiments, the film is an elastic film. In some embodiments, the change is volume reduction.

In some embodiments, the pressure inside the closed space is increased when the conductive element contacts or before, during or after the conductive element detects physiological sounds.

In some embodiments, the film is an elastic film. In some embodiments, the density of the gas molecules in the closed space is increased when the conductive element contacts or before, during or after the conductive element detects physiological sounds. The gas in the closed cavity is air, or any single gas or mixer of a variety of gases. In some embodiments, the conductive element is a hollow element, one end of the element is closed and the other end is open. In some embodiments, the open end is located on the thin film. The closed end is for contacting the skin of a mammal. In some embodiments, the end for contacting the surface of a living being is polygonal or round, and the open end is sealed with the thin film, thus to form a first cavity in the conductive element. In some embodiments, the cavity including the thin film is a second cavity, and the first cavity is communicated with the second cavity for treating fluid. In some embodiments, the first cavity or the second cavity includes gas, for example, air or a single gas. In some embodiments, the sealed cavity includes a gas substance for conducting sounds. The first cavity and the second cavity form a closed cavity. In some embodiments, the closed cavity is a gas-sealed cavity.

In some embodiments, the conductive element includes openings at both ends, the opening at one end is communicated with the gas in the second cavity, and the opening at the other end is communicated to the outside atmosphere;

when the conductive element detects the physiological sounds, if the element contacts the skin of a mammal or a human, the opening at the other end is sealed by the skin so as to make the second cavity in sealed state.

In some embodiments, the sound conductive element includes a first conductive element and a second conductive element, the first conductive element being located on the thin film and the second conductive element winding around the first conductive element. In some embodiments, the conductive element includes a closed end and an open end, the closed end for contacting a living being located in the second conductive element, and the open end communicated with the second closed cavity. In some embodiments, the first conductive element includes a first cavity, the opening of the first cavity and the second cavity form a closed cavity. In some embodiments, the opening of the first cavity the h the second cavity forms a closed cavity through the thin film. When the first conductive element contacts the skin of a mammal or a human, the second conductive element makes the first conductive element form a sealed space. This can reduce the interference from the outside.

In some embodiments, the thin film is either round, square or rhombic, and the sound conductive element is located at the center position of the thin film. In some embodiments, the thin film is round.

In some embodiments, the second cavity of the closed cavity includes a sound sensor, and the sound sensor corresponds to the sound conductive element. In some embodiments, the sound sensor corresponds to the first cavity.

In a further exemplary embodiment, the sensor comprises an air vibration sensor, a signal amplifier, an information converter and an external information interface, wherein the signal amplifier and the external information interface are connected with the information converter and the air amplifier is electrically connected with the signal amplifier.

In a further exemplary embodiment, the information converter converts the information acquired by the air vibrator to electric signals and transmits the information through the external information interface.

In some embodiments, the peripheries of the thin film protrude to the peripheries to form a third cavity, and a sealed cavity is formed when the opening of the third cavity contacts the surface. In some embodiments, the closed end of the conductive element is located in the third cavity.

The inventions provide a method for detecting physiological sounds, the method comprises providing a device for detecting physiological sounds, the device comprises a thin film, the thin film includes a sound conductive element, and the thin film is a part of the sealed cavity; making one end of the conductive element contact a body skin, so as to conduct the sound from the body in the living being onto the thin film.

In some embodiments, the conductive element is a sound conductive element in any of the above embodiments.

In some embodiments, the detection device is a detection device in any of the above embodiments.

Compared with the existing technology, the invention has the advantages that:

The invention has simple and reasonable design, strong practicability and is convenient for promotion and use. The overall structure design is smart and easy to operate, the heart sound is well amplified so as to enable general doctors to hear the hidden murmur and provide guidance for any possible illness condition; the invention can provide further accurate diagnosis for a patient to be further determined, greatly improving the level of general physical examination; the invention also can identify more hidden diseases and help patient be treated as soon as possible. From an overall view, the invention improves the reliability and anti-interference of heart detection while simplifying the operation method.

DETAILS OF DRAWINGS

Figure 11:
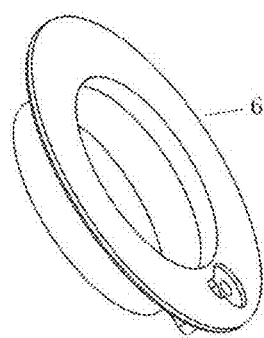
Figure 12:
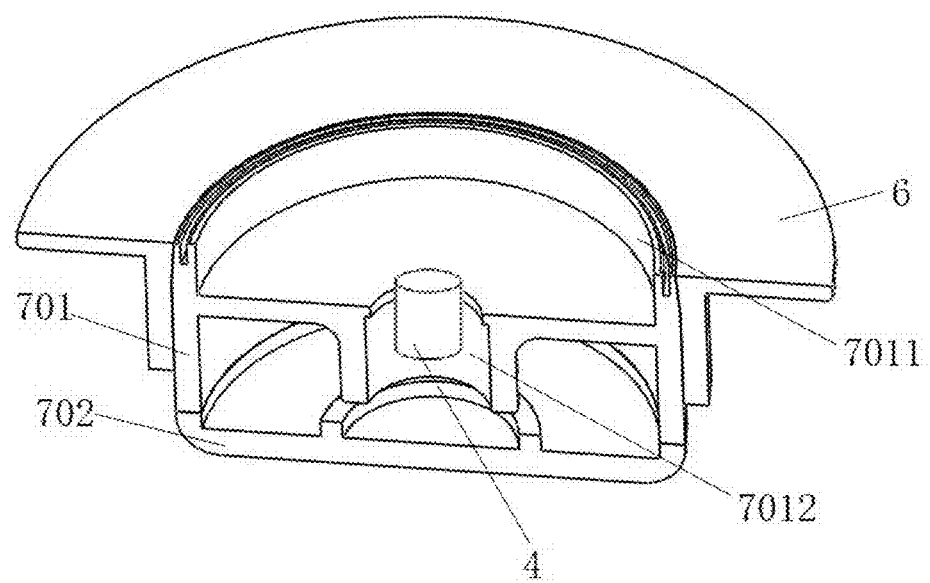
Figure 13:
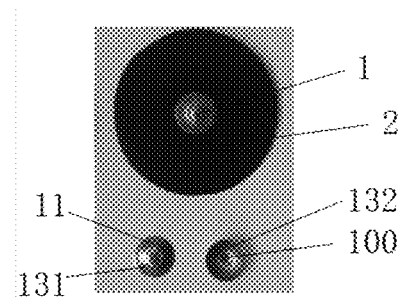
Figure 14:
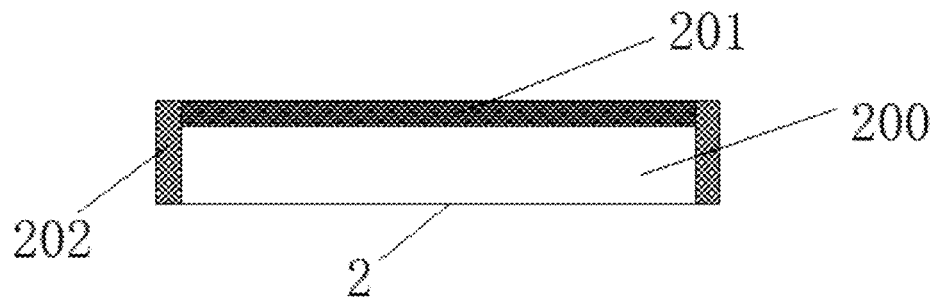
Figure 15:
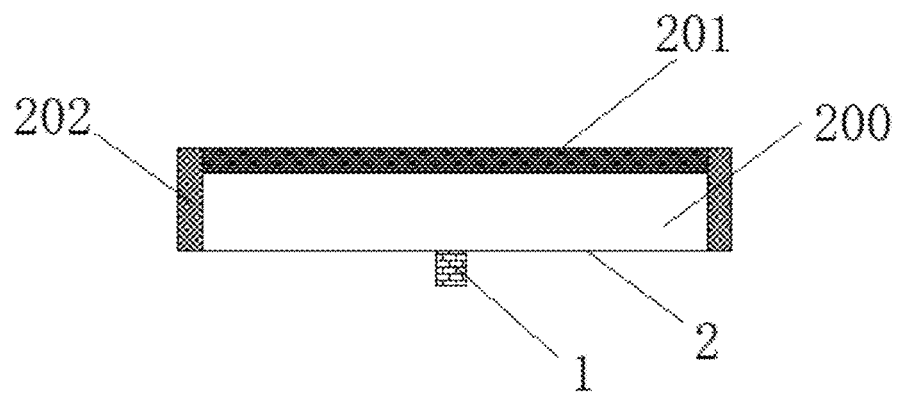
Figure 16:
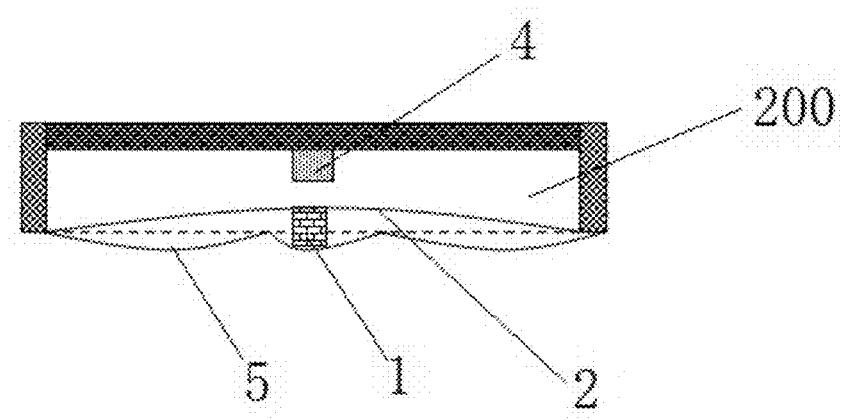
Figure 17:
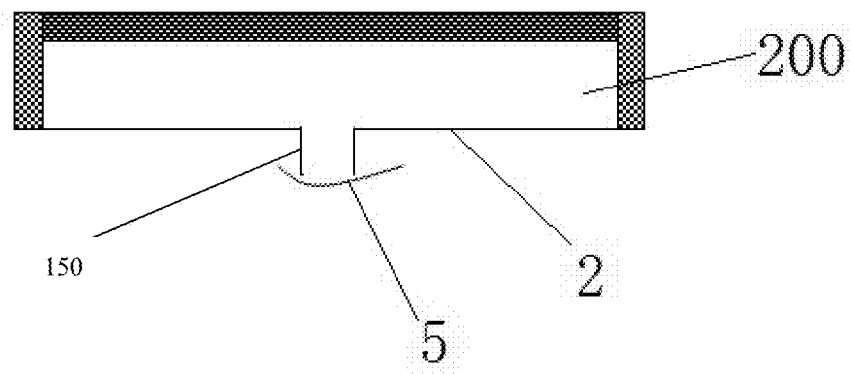

FIG. 11 depicts a stereogram of a component including a thin film for heart sound detection in a specific embodiment of the invention FIG. 12 depicts an assembly profile of a heart sound detection device in a specific embodiment of the invention FIG. 13 depicts a top view of an object including a thin film and a conductive element, wherein 131 is a top view of the conductive element and 132 is a bottom view of the conductive element FIG. 14 depicts a schematic diagram of a closed space not including a conductive element FIG. 15 depicts a schematic diagram of a closed space including a conductive element and a thin film FIG. 16 depicts schematic diagram of changes of the closed space when a conductive element contacts the skin of a living being FIG. 17 depicts a schematic diagram of a structure when the conductive element is bonded with the thin film through openings at both ends.

Figure 18:
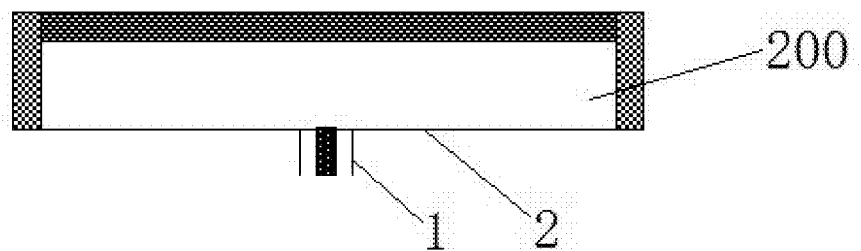

FIG. 18 depicts a structure in a specific embodiment of the invention, comprising a first conductive element and a second conductive element, wherein the first conductive element being located in the second conductive element; the first conductive element is sealed in a cavity by the second conductive element when the first conductive element contacts the skin, so as to reduce an interference from the outside.

Figure 19:

FIG. 19 depicts a crest chart of a position in the heart sound without a conductive element).

Figure 20:
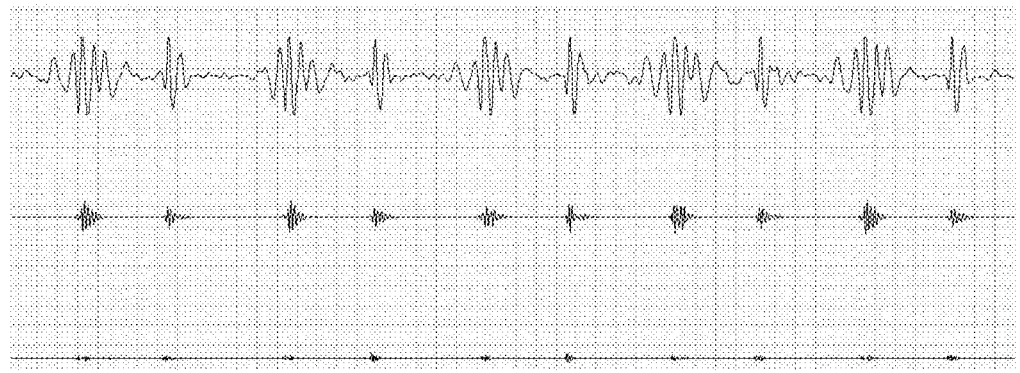

FIG. 20 depicts a crest chart of a position in the heart sound including a conductive element and the same position as shown in FIG. 19 (high frequency, medium and low frequency sounds from top to bottom).

Figure 21:
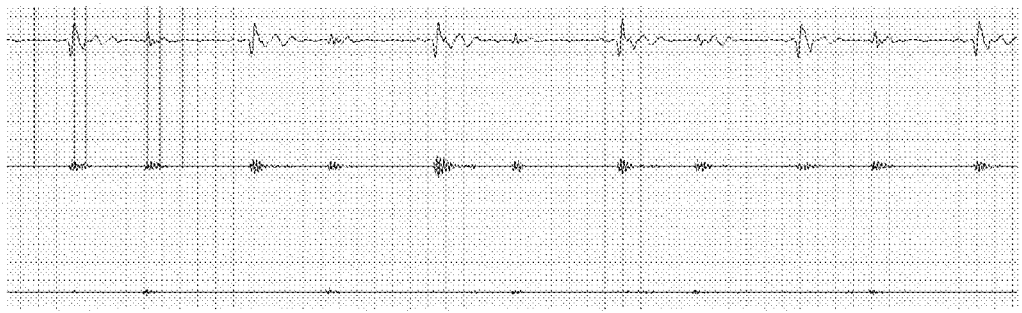

FIG. 21 depicts a crest wave chart of heart sound detection not including a ring.

Figure 22:

FIG. 22 depicts a heart sound chart including a metal ring (high frequency, medium and low frequency sounds from top to bottom).

Figure 23:
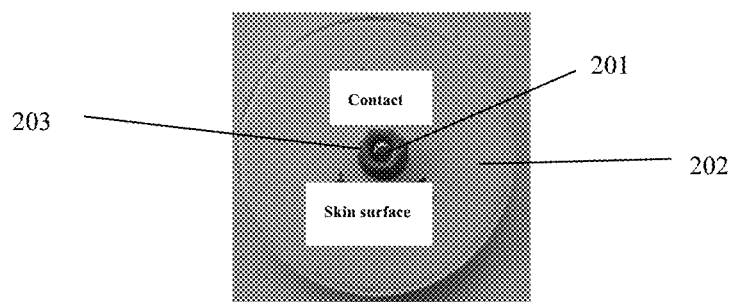

FIG. 23 depicts a physical picture including a ring on the thin film (a second conductive element), wherein a first conductive element 201 is arranged on the thin film 202, a second conductive element 203 in ring shape is arranged on the conductive element; the first conductive element is sealed in a space when the conductive elements contact the skin.

Identification in Figures: concentrator head 1, bottom part 11, energy-collecting part 12, first cavity 100, first cavity 101, second cavity 102, second cavity 200, rigid material 201 and rigid material 202, resonant thin film 2, limiting part 21, thin film covering a conductive element 22, fixed part 3, thin film fixing part 31, joining part 32, ring edge 33, base 34, connecting hole 35, anti-slide structure 36, sensor 4; skin 5; apron structure 6.

DETAILED DESCRIPTION

A Thin Film and Conductive Element

In traditional equipment for detecting physiological sounds, such as a stethoscope, when being used to hearing a physiological sound (a heart sound), making the thin film contact the skin surface, and then hearing the volume and change of a sound by ears. Stethoscope is a very traditional equipment for hearing sounds and has a number of disadvantages though still used by many doctors. Generally, experienced talents can accurately distinguish a normal sound from a pathological sound, and judge the severity of a pathological sound. Presently, many electronic equipment for detecting physiological sounds are developed gradually, such as a sound sensor; the equipment collects physiological sounds, converts the sounds into electric signals through a sensor, and then analyzes and filters the sound waves, recognizes the volume, change and occurrence time of the sound, judge whether the sound is normal, if the sound is not normal, a disease may occur. For example, the China invention patent (Patent No. 201310386451.9) uses a sound sensor to directly contact with the skin to collect a sound for detection. Insulated materials are provided on electrodes so that a vibration sound can be properly transmitted to a sensor, and the sensor then collects a sound directly.

Among many physiological sounds, the heart sound (the sound of a heart) receives much concern. If the heart sound is abnormal, it often indicates that some functions of the heart cannot be performed properly, showing an early symptom of the heart which can be prevented in advance. Of course, in addition to a heart sound detection, the device can also detect the sound of other physiological organs, such as the sound of a lung or an intestine.

However, the inventor of the present invention found that when a sound sensor is used to detect a physiological sound, if the conducted sound is collected first, the sound can be amplified with a physical method; the sound sensor can sense a stronger vibration so as to identify a minor change of the sound and facilitate early diagnosis of a disease in an organ. The team of the invention accidentally found that adding a sound conductive element to the thin film of a traditional stethoscope can amplify a sound. The amplified sound is converted into an electronic signal through the sound sensor to allow digital detection of physiological sounds.

Generally, a sound of a physiological organ is caused by the internal physiological changes of the organ, for example, the sound of a heart is closely related to the movement of the heart, and the movement of the heart is directly related to the generation of ECG. The following gives details, in particular to details of production and changes of a sound. The relaxation and contraction of the heart are accompanied by the flow of blood, and the flow of blood through the heart is accompanied by the production of the sound. This is called the heart sound. The invention additional provides a sound conductive element to a traditional stethoscope, which can amplify a physiological sound, and an electronic component is used to perform automatic recognition and calculation, automatic monitoring or diagnosis, so as to achieve automatic monitoring or diagnosis.

Therefore, in some embodiments, providing a cavity, the cavity comprises a thin film and the thin film is a part of the cavity, the cavity is a closed cavity and includes air inside, and the air can conduct a sound. For example, in a more specific structure, the structure in FIG. 1, the structure comprising an empty cavity 200, the cavity is surrounded by multiple surfaces, wherein a surface is provided with a thin film 2, and sound conductive element 1 is arranged on the thin film. The cavity 200 is a closed cavity, the so-called second cavity includes air inside, and the air can transmit a sound. The conductive element has a closed en 12 and an open end. In the embodiment, the conductive element has a hollow structure, forming a first cavity 100. The first cavity 100 and the second cavity 200 form an integral sealed cavity. The combination of the thin film and the conductive element form a number of preferred embodiments, for example, making a small hole in the thin film 2, the size of the small hole being suitable for the opening at the other end of the conductive element, so as to enable the opening end of the conductive element to go through the small hole and then seal the gap between the thin film and the conductive element. To make it simpler, the conductive element has a structure like a hat comprising a hat brim 11, or has an apron-like structure, the structure has a large surface, the surface can be used to bond with the thin film, so as to form the structure shown in FIG. 1. At this moment, the thin film covering the opening of the conductive element may exist or not exist, if the thin film does not exist, it means that small holes exist in the location on the thin film that corresponds to the opening of the conductive element on the thin film. In some embodiments, the material density of the conductive element is higher than the density of the thin film. Generally, the thin film that allows a sound to cause vibration is used, the thin film, such as some PVC, PCP or other similar films that can cause vibration, the vibration is caused by a sound. Of course, a thin film similar to the one used on a traditional stethoscope can also be used. When detecting physiological sounds, making the closed end 12 of the conductive element to contact the skin of a living being, so as to detect the sound produced by the organ as the organ is underneath the skin. In some embodiments, the conductive element protrudes relative to the thin film. The bump height may be 1 mm, 2 mm, 3 mm, 4 mm, 5 mm, or 10 mm.

In an embodiment, the device is used to detect a heart sound, making the closed end 12 contact the skin of a chest and the location of the heart is just beneath the skin of the chest. The biggest difference from a traditional stethoscope is that the stethoscope makes the whole thin film contact the skin, whereas the invention only makes the closed end of the conductive element 12 contact the skin. It can be seen from the above, the area in contact with the skin is greatly reduced, we are surprised to find that the device can be used to amplify the physiological sound and have a more accurate detection. This will be described in detail later. Therefore, in an embodiment, the area of a conductive element of the invention in contact with the surface or the skin is smaller than the area of a thin film. When the conductive element protrudes relative to the thin film, vibration is conducted when contacting the skin, the thin film may not contact the skin or the thin film may not wholly cover the skin, or not actually cover the skin, or only partially cover the skin.

As a matter of fact, the heart sound detected above is an indirect sound. This is because the heart is located in the chest, The relaxation and contraction of the heart causes the flow of blood, and the flow of blood is from a large blood vessel into a heart ventricle and a heart atrium, and the heart ventricle and the heart atrium have valves, the valves close and open mechanically to control the flow of blood, this is bound to cause physiological sounds, and the sounds are transmitted to the surface of the skin through a subcutaneous tissue.

The sound is transmitted in the form of waves, and this way of transmission can cause vibration, the transmission of the heart sound can cause vibration of the skin, making the thin film in contact with the skin is to transfer such vibration the thin film to cause the vibration of the thin film, so as to make the ears of a human hear or detect through a sound sensor the change of the heart sound.

Making the whole thin film contact the skin or putting the conductive element in contact with the skin has substantial difference in transmission of a sound. The difference in effect may be caused by the following factors: on the one hand, the area of the thin film in contact with the skin is significantly larger than that of the conductive element. In this way, the reduced contact area only enables the conductive element to feel the vibration of a small area so that the disturbance on the vibration is minimized. This may be caused by transmission of the heart sound through the subcutaneous tissue, the subcutaneous tissue is heterogeneous, and the subcutaneous tissues have different densities, in this circumstance, when the sound is transmitted from the heart beneath the skin or to the skin surface, not all positions on the skin have the same vibration frequency; if making the thin film contact the skin at this moment, the thin film may have a different vibration frequency, if the thin film is made of the same material, the sound wave that causes the thin film frequency resonance is always at the same frequency, while sound waves of other frequencies may cause interference, this will allow the thin film to contact the skin in a large area to collect the possible frequencies of the sound, the so-called multi-frequency collection. Or when the material of the thin film is the same, while the vibration sensed at different position of the thin film is different, then vibrations of different frequencies exist on the thin film, and only a high vibration can be heard, because vibration can cause a second vibration of air, several different vibrations may cause vibrations in different parts of the air, but the vibration of air is messy, only if a sensor is used to receive the vibration of the thin film, the vibrations are still at variety of vibrations in different frequencies, thus to obtain messy sound waves with mixed frequencies; although the heart sound varies in high, medium and low frequencies, but for a sound wave with mixed vibration frequencies, the detection background may be enlarged, while the slight and weak sound might be ignored. Conversely, making the small area of the conductive element contact the skin surface, only a lowest single point vibration can be sensed, enabling the conductive element to transfer such single point vibration onto the thin film, the vibration on the thin film may not only include the single point vibration, the vibration of the air caused by the single point vibration is also of a single frequency; when a sensor is used to detect the sound wave, only the vibration of a single frequency is obtained, thus to reduce the interference from other frequencies. Wherein the single frequency does not mean only one frequency, it is a relative concept when the thin film contacts the skin in a large area. In this way, the point of the sound wave obtained by the sensor is specific, the sensitivity is increased and the weak sounds can be recognized. Wherein the area of the conductive element in contact with the skin can be $1/2$, $1/3$, $1/4$, $1/5$, $1/6$, $1/7$, $1/8$, $1/9$, $1/10$, $1/12$, $1/13$, $1/15$, $1/20$, $1/40$, $1/50$, $1/100$ of the area of the thin film or any other proportion.

Closed Space

Another important factor may be a volume change in a closed space. Compared with the traditional, when the whole thin film contacts the skin, the volume of the closed space 200 formed on the thin film may not be substantially changed, the air density of the closed cavity may not be substantially changed, and the vibration of the thin film needs to be transmitted via air. The invention uses a conductive element, the conductive element, on one hand as mentioned above, has a reduced contact area with the skin. On the other hand, when the conductive element contacts the skin, the conductive element and the skin have to bear a certain pressure, the pressure is generated by close contact between the conductive element and the skin, the vibration can be conducted to collect a stable sound wave. However, when the conductive element closely contacts the skin, the conductive element surely imposes a reserve force on the thin film to make the thin film move inward, thus to reduce the volume of the closed space, the reduction of the volume can lead to reduction of the air volume, relative to the initial status of the thin film, the air is compressed, and the density is increase after air compression. Sound waves can be transmitted through air, while the volume of air decreases and the density increases, thereby increasing the effect of sound wave transmission. If the sound sensor is placed in a sealed space, the current signal sensed can be significantly enhanced. Therefore, another essential characteristic of the present invention is that the volume of the second closed space is reduced when the conductive element is in contact with the surface of a living being. Then, the volume of the sealed space is compressed, and the air density of the enclosed space is increased. Of course, it can be concluded that when a thin film is taken to contact the skin without the need of a sound conductive element, if the thin film can be changed to reduce the volume of the enclosed space, then the compressed air certainly can exert a good effect. Therefore, the present invention provides a second solution, a device for detecting sounds comprises a closed space, the closed space is provided with a thin film surface, When the thin film contacts with the surface of a living being to test the sound of the organs of the living being, the volume of the closed space decreases, thereby compressing the air in the closed space. The compression can be, for example, the above compression with a conductive element, or a compression by another method, if the volume of the closed space formed by the thin film is reduced when the thin film is sensing or transmitting sound waves, the density of the air can be increased. Of course, the case can also be that the volume of the closed space remains unchanged, but the density of the air increases, for example injecting more air from another position, so as to increase the density of the air per unit volume.

The so-called closed space refers to the closed state of the space during detecting or preparing for detection. When the conductive element contacts the skin of a human or a mammal, or before the conductive element contacts the skin of a human or a mammal, the space is a closed state. When the space is being closed, the air or gas content in the space is substantially determined, but the volume of the closed space can be changed, for example, reduction of the volume. Either increasing of air in the closed space or increasing of air density can achieve the effect of relatively enlarging the sound of the invention. When the thin film is elastic, the volume of the above closed space is reduced. If the thin film is not an elastic film, before or during detecting, inflating air in the space can increase the density of the gas molecules. As shown in FIG. 17, before detection, the space is non-closed, during detecting or preparing for a detection, an open end of the conductive element 150 is put in contact with the skin surface of a human or a mammal, to form a closed space, the thin film 2 and the conductive element can still conduct sounds.

For example, comparison of a closed space as shown in FIG. 14 to FIG. 16; forming a closed space 200 as shown in FIG. 13, the closed space is mainly formed by rigid materials, while the thin film 2 has certain elasticity. When the whole elastic thin film contacts the skin, the volume of the closed space cannot be compressed; the compression may be very small and can be ignored even if there is. However, as shown in FIG. 14, expect for the same structure as shown in FIG. 13, a raised conductive element 1 is arranged on the thin film 2, the conductive element 1 has rigidness as compared with the thin film 2, because the conductive element has a small bump and the bump cannot cause elastic deformation, but for the thin film, it can cause deformation of the thin film, and lead to vibration, thereby obtaining a sound wave or a sound of a certain frequency. When being used, one end of the conductive element 1 contacts the skin 5, general the element should closely contact the skin, so as to apply a pressure to the conductive element, and the pressure can be applied to the skin contacted during the detection, and indirectly applied through other rigid material 201 or 202 of the closed space. Due to the elasticity of the thin film, the conductive element reacts on the thin film, the skin is under the pressure applied by the conductive element, and the conductive element also applies a pressure to the thin film, then the pressure causes the thin film to press into the closed space, so as to reduce the volume of the closed space but the air content in the closed space remains; when the volume is small, the density of air molecules can increase, the sound conducted from the conductive element 1 causes vibration of air molecules in the closed space, thereby achieving transmission of sounds (as shown in FIG. 16). The closed space is provided with a sound sensor 4 to sense a sound transmitted by air. Then the sound is converted to an electrical signal for further analysis, for example, filtering, division of high, low and medium frequencies, and analyzing the high, low and medium frequencies. The air above mentioned can also be replaced by other gas molecules, such as a single gas molecule, a carbon dioxide molecule, a nitrogen molecule, an oxygen molecule; while air is preferred.

In a preferred embodiment, a first cavity 100 is arranged on the conductive element, when the thin film deforms and presses into the closed space, the first cavity 100 corresponds to a sensor, a part of the sensor can enter the first cavity 100 but not contact with the thin film and the conductive element, so as to save space and better sense or sense the changes in the sound more closely, thereby guaranteeing more sensitive detection.

As we know, sound is a pressure wave; when playing a musical instrument, taping on a door or knocking a table, the sound vibrations cause, the medium-air molecules, to vibrate rhythmically, cause change in the density of the surrounding air, producing an alternating longitudinal wave, thus a sound wave is created, and such phenomenon continues until the vibrations disappear. As a kind of wave, sound can always be decomposed into superposition of sine waves of different frequencies and intensities. The process of transformation (or decomposition) is called the Fourier Transform. Hence, a general sound always includes a certain frequency range. A human ear can hear the sounds in a frequency range of 20 to 20,000 HZ. The waves below the range are called ultrasonic waves, and the waves below the range are called infrasonic waves.

A sound travels in different media at different speeds. The speed at which a sound travels is related to the counterbalancing force of the medium, counterbalancing force means when a molecule of a matter deviates from its equilibrium position, the surrounding molecules push the molecule back to the equilibrium position; the greater the counterbalancing force, the faster the sound travels. In addition, the transmission of sound is also related to a resistance. In windy weather, a sound always travels much slower. A sound is also reflected by an external obstacle, for example, when a person shouts to the mountains, he can hear his own echo. The example of refraction means that a sound travels farther at night than it does in the daytime, because when the sound travels in the daytime, it encounters a rising hot air, and the air quickly refracts the sound into the air; when the cold air descends at night, the sound spread slowly and calmly on the surface, which is not prone to refraction.

The sound transmission size is directly related to the medium. For example, sound travels through the air, when the air is dense with molecules, sound travels faster in the air, and the loss in sound size (decibels) is smaller; conversely, when the air is less dense with molecules, sound cannot travel faster in the air, and the loss may be larger, and the resulting sound can be different from the sound produced by the source. The present invention follows the principle to collect the sound produced by some organs of a living being or by some organs in different working conditions, and amplify the sound through a physical method, for example, reducing the volume of the closed space, increasing the density molecules in air, decreasing the loss of sound transmission, thereby making the sound obtained from the sensor relatively more sensitive. When the organ produces a certain sound, the transmission of sound is directly related to the medium. The present invention uses the technology to indirectly amplify the physiological sounds.

The present invention provides two independent proposals, wherein one proposal is making the thin film contact the skin to reduce the transmission vibration points, thus forming a single-point contact, for example, making one end of the conductive element contact the skin. Another independent proposal is increasing the density of the air in the closed space when feeling or transmitting the vibrations, so as to increase the transmission effect of vibrations. One proposal to increase the density of air in the closed space is compressing the closed space, and reducing the volume, thereby increasing the density of air. Of course, it can also be a combination of the two proposals. For example, as shown in FIG. 1 to FIG. 7, the conductive element is located on the thin film, so that the contact area of the thin film with the skin can be reduced, and also the closed space can be compressed during the detection.

In some preferred embodiments, for example, as shown in FIG. 17, the conductive element is a rigid material and openings are arranged at both ends, one opening communicated to the closed cavity and the other to the outside. Others are the same as the structure as shown in FIG. 16. When detecting a sound, making the open end of the conductive element to the outside contact the skin, so that the contacted skin can seal the opening, thus to close the space 200. The conductive element can still conduct skin vibrations, and the skin that seals the opening also vibrates, thereby causing the vibration of the thin film. For similar reasons, the thin film is generally elastic, due to the effect of the pressure; the volume of the closed space is reduced, thereby amplifying the sound. Actually this sealing only transmit partial vibrations of the skin that has the sealing effect through air, but the external sound, such as the vibration or sound in the environment, cannot cause interference to the transmitted vibration; sounds in the environment such as mechanical noise, the breathing sound of a tester, as well as the current sound of testing equipment, sound of operating the button of the testing equipment, cannot come to the surface of the skin sealed by the opening at one end of the conductive element and affect the vibration of the skin. Thus, the interference to the tested sound is reduced, thereby obtaining a higher sound wave and wave crest.

Figure 1:
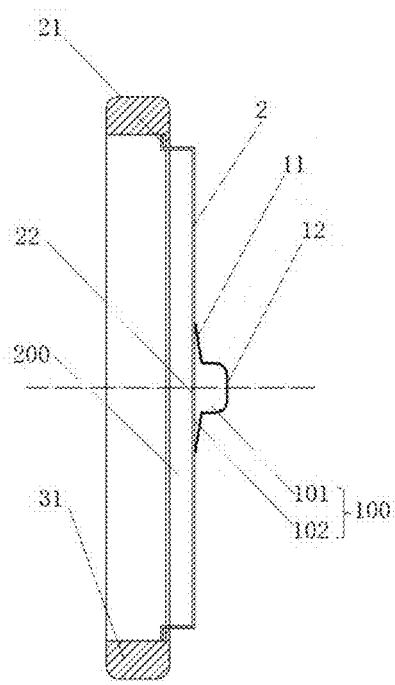
FIG. 1 depicts a combined side view of a concentrator head, a resonant thin film and a fixed element of the invention.
Figure 2:
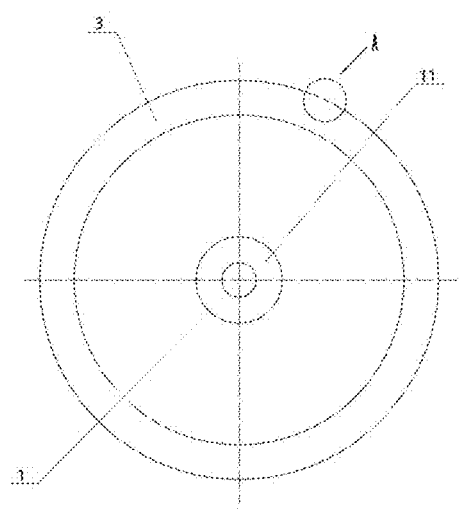
FIG. 2 depicts a right view shown in FIG. 1 of the invention.
Figure 3:
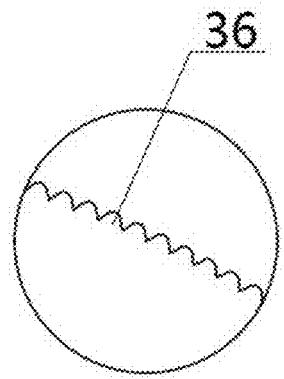
FIG. 3 depicts a partial enlarged drawing of part A shown in FIG. 2 of the invention.
Figure 4:
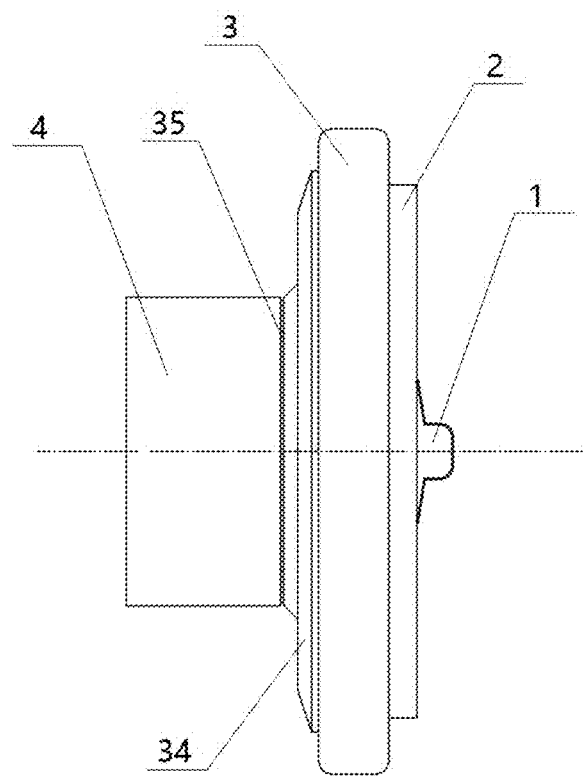
FIG. 4 depicts a structural diagram of the invention.
Figure 5:
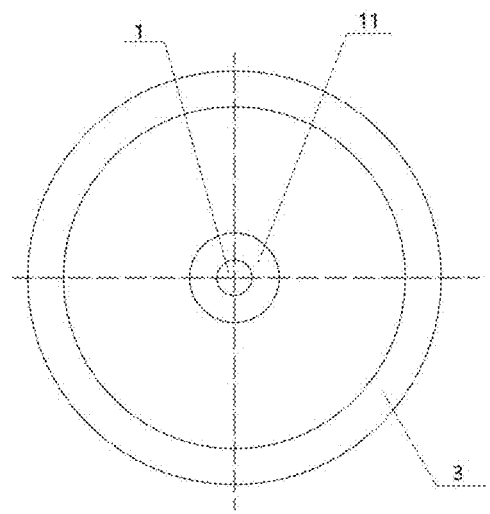
FIG. 5 depicts a right view of FIG. 4 of the invention.
Figure 6:
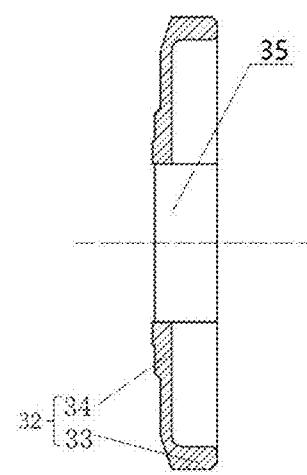
FIG. 6 depicts a schematic diagram of the ring edge and base of the fixed element of the invention.
Figure 7:
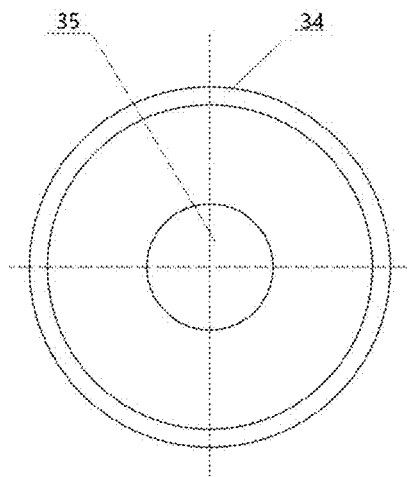
FIG. 7 depicts a left view of FIG. 6 of the invention.

In another embodiment, as shown in FIG. 6 and also FIG. 1 and FIG. 23, a metal ring is covered over the conductive element as shown in FIG. 1, the conductive element is bonded with the thin film, and the metal ring is located outside the conductive element and encloses the conductive element. The height of the metal ring is equal to or substantially similar to that of the conductive element. When the closed end of the conductive element contacts the surface of the skin, the metal ring also contacts the skin, so that a closed space is formed around the conductive element, and the metal ring actually has the effect of isolating the external sound, the conductive element can conduct the vibration of the skin to the largest extent, reduce the influence of the external noise and also interference, thereby accurately detecting the vibration of the skin. The metal ring can be other materials, such as plastic material, alloy, wood, and the materials are mainly used to reduce the interference with the conductive element from the external or environmental non-physiological sound.

Figure 10:
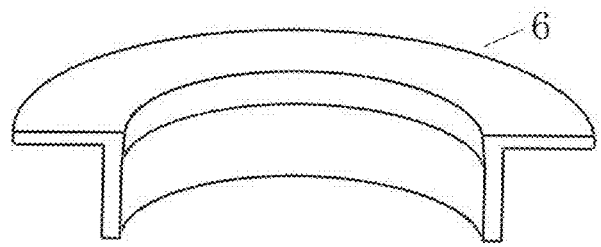
FIG. 10 depicts a cross-sectional view of the stereogram of a component including a thin film for heart sound detection in a specific embodiment of the invention (not including a thin film and a conductive element)

In some other embodiments, as shown in FIG. 11 to FIG. 13, the closed space includes two part, for example the apron structure 6 in FIG. 10 and the component 701 and 702 assembly as shown in FIG. 12; 701 is actually a cavity structure, comprising one end opening 7011 and the other end including a through hole 7012, an apron structure 6 is covered on the outer surface of the cavity, and is sealed by a thin film 2 (FIG. 13) on the opening of the cavity, and the through hole 7012 at the other end comprises a sound sensor 4, the sensor 4 seals the through hole 7012, so as to form a closed space. A metal element is arranged on the PVP thin film 2, for example the conductive element made of aluminum alloy in a button shape, a apron 11 is provided on the conductive element 1 and bonded with the thin film, the thin film is provided with an opening at the inner side of the corresponding element, and the opening is communicated to the cavity 100 in the conductive element. The present invention is used to detect the heart sound of the same person at the same position, compared with the detection made by a device comprising only a thin film and without a conductive element, the wave crest of the heart sound is enlarged, the position of the sensor is in the detecting device and the computation process in FIG. 19 to FIG. 22 are the same, as well as the thin film, only the presence of a conductive element and the change of the design mode causes the change in the wave crest of different heart sounds in high, medium and low frequencies. For example, FIG. 19 shows a wave crest diagram of a certain position of the heart sound without a conductive element, and FIG. 20 shows a wave crest diagram of the same person at the same position with a conductive element. It can be seen from FIG. 19 and FIG. 20, the wave crest is significantly higher, having a significant amplification effect.

In another embodiment, compared with FIG. 21 and FIG. 22, the thin film is still the same PVC film, a metal ring is covered over the conductive element, as shown in FIG. 21. The other structures are the same as shown in FIG. 10-FIG. 12, the same person is tested at another position, it was found that the wave crest of the heart sound at the same frequency with a ring rose and the external interference was reduced. FIG. 21 shows a wave crest diagram of the heart sound without a ring but with a conductive element; FIG. 21 shows a heart sound diagram with a metal ring, it was found that at the same position of the same person, amplifying effect can be obtained, crests are cleaner, it may be because the ring reducing the interference of the outside world, specific analysis may be made, but it can be sure that the heart sound is really amplified.

According to the analysis of the above principles, the general technical personnel can freely choose the material and structure of the thin film and the conductive element when seeing the content of the present invention. The conductive element can be hollow as shown in FIG. 1, or solid The conductive element can be made of the same material as the thin film or different materials. Having a hollow or having a brim is only a preferred proposal for assembly. The thin film can be an elastic thin film or a thin sheet if only it can well transmit a sound or vibration, for example, plastic material, fiber, sheet metal, etc. The conductive element can also be made of plastic material, fiber, metal, etc. In addition, in some embodiments of the invention, the conductive element is made of a metal material or some conductive materials, so as to detect ECG This is only a preferred proposal.

When using a conductive element to detect the heart sound, the vibration senses by the conductive element is transmitted to the thin film, so that the thin film and the conductive element both vibrate; the vibration frequency of the sound wave is transmitted through the air the sound sensor, thereby achieving change of an electronic signal. Instead of a sound sensor, the vibration frequency can also be transmitted directly to a human ear, for example, a doctor's ear, so as to carry out direct auscultation.

In some other embodiments, the conductive element can have a closed end and an open end, or adopt other structures, such as a hollow column with an opening at both ends. In some proposals, a conductive element protrudes out of the surface of the thin film, so that when the conductive element contacts the skin, the thin film does not contact the skin or does not substantially contact the skin. In this way, when the conductive element contacts the skin, pressure may be generated and make the thin film concave into a closed space, thereby compressing the volume of the closed space. Therefore, the elasticity of the thin film and the bump size of the conductive element can be reasonably matched.

In other embodiments, a closed space can be in any shape if only the volume of the closed space can be changed during transmission of a sound, so as to change the speed of sound transmission and reduce the loss of sound transmission, thereby guaranteeing the consistency with the sound source and reducing the loss. In addition, the closed space can include air, but also other single-molecule gases, such as merely oxygen, nitrogen, carbon dioxide or other gaseous materials.

Sound Sensor

The sound sensor herein is an electronic component for sensing a sound. In an embodiment, the sound sensor can sense a sound in the closed air, and carry out conversion from a sound signal to an electronic signal, division of frequencies and elimination of noise together with some other electronic components, also including some calculation schemes for working out the required sound signal. This can be solved by the existing technology. Besides a sound sensor, the device can also include some other electronic components for digital detection and detecting, so as to achieve detection of a heart sound.

When a conductive element is metal, the conductive element can be used to detect ECG, then the metal element has a dual function, transmitting sounds and conducting ECG, functioning as contactor to detect ECG; in this way, the element can detect both the heart sound the ECG, and obtain more results from analysis of the heart sound the ECG data, thereby predicting the risk for more patients, including a heart failure.

Physiological Sound and Detection

The so-called "physiological sounds" generally refer to the sounds in a mammal and a human, including the sound of various organs, such as a lung sound, a heart sound, an intestine sound, a pulse sound. In some embodiments, the physiological sounds refer to the sound made by the heart. The production and changes of the physiological sounds are directly related to the functions of organs. When functions of these organs go wrong, changes of sounds will be inevitably caused; the test or detection of sound changes can directly reflect the health status of organs. In particular, when an organ has early lesions, generally it is not easy to detect, and the optimal treatment period may be missed. The device for detecting physiological sounds of the present invention can significantly improve the sensitivity of detection; accurately distinguish the early weak sound from the diseased organs, thus indicating the possibility of pathological changes of the organ, so that detecting of other indicators can be conducted further in a timely manner.

A heart sound is the sound made by the heart. A heart sound is the sound produced by vibrations caused by contraction of the heart muscle, closure of the heart valves, and blood hitting the walls of the ventricles, great arteries, etc. Formation of a heart sound refers to that each cardiac cycle produces four heart sounds, and generally a first and a second heart sound can be heard. The first heart sound occurs during cardiac contraction, marking the beginning of a ventricular systole. It can be heard most clearly at the apex pulsation (medial to the midline of the left clavicular in the 5th intercostals space of the anterior chest wall) The sound has a low tone (40-60 hz), and lasts long (0.1-0.12 seconds), and hears loud. Causes: 1. Vibration of the ventricular wall caused by blood flow rapidly colliding with the atrioventricular valve during ventricular contraction; 2. Vibration caused by the closure of the atrioventricular valve and tension of the valve blades and chordate. 3. The vibration is caused by the ejection of blood from the ventricle against the wall of the aorta and the pulmonary artery. The first heart sound can be louder if the ventricular contractility is stronger. A first heart sound is produced by various mechanical vibrations in the ventricular systole, starting from the time when the atrioventricular valve closes and ending before the semilunar valve closes. Wherein, myocardial contraction, valve opening and closing, and the pressure application and relief effect of blood flow on the vessel wall can all cause mechanical vibrations, and thus participating in the formation of heart sounds. However, the magnitude of vibrations produced by various activities may be different; the effect of valve closing is the most obvious. Therefore, the main component of the first heart sound is atrioventricular valve closing.

A second heart sound occurs in the heart relaxation period, marking the beginning of ventricular diastole. The tone is high and the duration is short, the semilunar valve closes the vibration and the blood flow impacts on the arterial wall. It is divided into two components: aortic sound and pulmonary artery sound, and can be clearly heard in the auscultation area of aorta and pulmonary artery respectively (the second intercostals space of the right and left margin of sternum). It is caused by the rapid closing of the aortic valve and pulmonary valve, the impact of blood flow, and the vibration of the root of the aortic and pulmonary arteries and the inner wall of the ventricle. The tone is high (60-100 hz), the duration is short (0.08 s), and the loudness is weak. Its strength can reflect the situation of the aortic pressure and pulmonary arterial pressure; the second heart sound can accentuate when the arterial pressure increases. A third heart sound occurs after the second heart sound, the duration is very short (0.04-0.05 s) and the tone is low. It occurs in the early ventricular diastole period, with the opening of the atrioventricular valve, the blood in the atrium and the pulmonary vein quickly flows into the ventricle (before atrium contraction), causing the ventricular wall and chordae tendineae vibration. The sound cannot be necessarily abnormal if it can be heard in most children and about half of the young. A fourth heart sound is a low-frequency vibration that occurs before the first heart sound, and it lasts for about 0.04 seconds. It is vibration caused by atrial contraction, and rapid filling of blood in ventricular, also known as atrial sound. Most healthy adults can have a record of a low fourth heart sound on a phonocardiogram, which is usually difficult to be detected by auscultation. It is a low frequency vibration, and its formation may be related to atrial contraction and early rapid filling. It is normal to hear the third and the fourth heart sounds in a child, but is a pathological phenomenon if heard in an adult. After a heart valve is diseased, abnormal vibration and change of blood flow may happen to the valve, thus producing abnormal heart sound, called heart murmur.

Differences and similarities between the first heart sound and the second heart sound Characteristics of a heart sound; main reason for the formation; the first heart sound; beginning of ventricular contraction; low tone; long duration; ventricular muscle contraction; closing of atrioventricular valve; the second heart sound, high tone, short duration; semilunar valves closing vibration; blood flow impacting the vibration of arterial wall; 2. The formation mechanism of the first heart sound and the second heart sound: (1) The first heart sound is produced by various mechanical vibrations in the ventricular systole, starting from the time when the atrioventricular valve closes and ending before the semilunar valve closes. Wherein, myocardial contraction, valve opening and closing, and the pressure application and relief effect of blood flow on the vessel wall can all cause mechanical vibrations, and thus participating in the formation of heart sounds. However, the magnitude of vibrations produced by various activities may be different; the effect of valve closing is the most obvious. Therefore, the main component of the first heart sound is atrioventricular valve closing. (2) The second heart sound is produced by various mechanical vibrations in the ventricular systole, and the main components are semilunar valves. 3. Third heart sound and fourth heart sound It is a low frequency vibration, and its formation may be related to atrial contraction and early rapid filling. It is normal to hear the third and the fourth heart sounds in a child, but is a pathological phenomenon if heard in an adult.

How to diagnose abnormal heart sounds: first, detect or monitor the heart sounds, and the biggest obstacles lies in the heart sound has high occurrence frequency, low sound frequency, and short duration; it is necessary to transmit the sound detected in a short period of time to the detecting equipment, so the transmission speed should be high; if transmission speed is higher, more accurate detection signals can be detected; in addition, if the sound can be enlarged on the condition that the heart sounds can be heard, then some abnormal sounds (noise) can be found, so that early diagnosis can be provided. The present invention can solve the above technology problem, improvement of the detecting device accelerates the transmission of sound, the invention enlarges the sound by a physical method before the sound is detected by a sensor when transmission the sound, thereby achieving enlargement of sounds, reducing the loss of sound transmission.

A Method for Detecting Physiological Sounds

The invention provides a method of physiological detection, the method provides a detection device, comprising a thin film, a conductive element is arranged on the thin film, putting the conductive element in contact with the part to be detected, and making the thin film change.

In some embodiments, the thin film is a part of a closed space, the volume of the closed space is compressed when the conductive element contacts the part to be detected. In some embodiments, the closed space includes a gas that can conducts sounds, for example, air or other gases.

DETAILED DESCRIPTION

Combining the drawings and the detailed description, the inventions are further described as follows.

Figure 8:
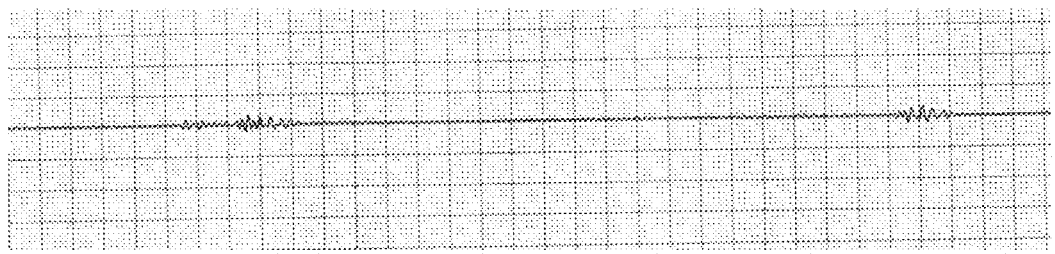
FIG. 8 depicts a monitoring ECG of a traditional stethoscope.
Figure 9:
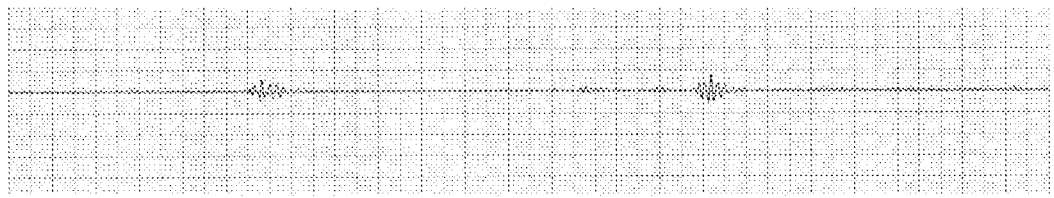
FIG. 9 depicts a monitoring ECG of the invention

As shown in FIG. 1 to FIG. 7, a new human physiological information monitoring equipment, comprising a concentrator head 1, and a resonant thin film 2; wherein the concentrator head 1 is arranged on the resonant thin film 2, generally the concentrator head 1 is arranged at the central position of the resonant thin film 2, the head can concentrate heart sounds, and the effect is better if putting it at the central position. As shown in FIG. 8 and FIG. 9, different ECG amplification effects monitored by using the stethoscope of this proposal in external monitoring equipment, in the same unit specification, with the same monitoring object at the same time; and in the external monitoring equipment, the stethoscope has stronger anti-interference and can better distinguish from various frequency band signals.

A first cavity 101 is formed between the bottom part 11 of the said concentrator head 1 and the resonant thin film 2.

As a preferred embodiment, a new device for monitoring human physiological information also includes a fixed element 3, a sensor 4 and a data transmission structure. The fixed element 3 includes a thin film fixed part 31 and a joining part 32, the resonant thin film 2 is arranged on the thin film fixed part 31, the sensor 4 is arranged in the center area of the joining part 32, the section size of the sensor 4 corresponds to that of the concentrator head 1 and generally slightly smaller than the concentrator head 1, so that the signals to be collected can be obtained as possible. The distance between the sensor 4 and the concentrator head 1 is 0.5 cm to 3 cm. The data transmission structure is connected with the sensor 4. Transmission of heart sounds can be maximized through the sensor 4.

The said concentrator head 1 comprises a bottom part 11 and a concentrator part 12, wherein the bottom part 11 is polygonal or round, and the peripheries of the bottom part 11 gradually protrudes towards the center to form a second cavity 101 with the resonant thin film 2, so as to collect the heart sounds through the concentrator head 1 and gather the sound at a position, achieving the maximum resonance effect. The said concentrator part 12 is in a cylinder shape, either a polygonal cylinder or a circular cylinder, and it is located at the highest point of the whole concentrator head 1, being 0.3 cm to 4 cm higher than the highest point of the resonant thin film 2. This can form a convex focus point, maximizing the resonance effect at the focus point. The concentrator head 1 is an integral whole, generally made of a metal solid material, so as to achieve the fastest resonance transmission speed, the least consumption, thereby reflecting the actual situation most accurately. The said concentrator part 12 can also be in a hollow cylinder shape, forming a second cavity 102, and the second cavity is communicated to the first cavity 101 formed by the bottom part 11; compared with a solid concentrator part, the effect may be not very good, but there is no great different, and this can reduce the production cost, and it is easier to hold the concentrator head 1, thereby achieving good using effect and longer using time when being used by a doctor. In the two embodiments, a hollow cavity can be formed, so that vibration through the air can easily cause vibration of the resonant thin film 2. At present, auscultation equipment is not provided with a concentrator head 1, so the resonance effect caused is very small; but this embodiment improves the effect by at least five to six times Although an experienced expert doctor can also hear possible problems after using the existing auscultation equipment, the stethoscope of this proposal is provided with a concentrator head 1 and the concentrator head can amplify the heart sounds, so that even an ordinary doctors can accurately hear the murmur in the heart sounds, thereby greatly promoting the accurate diagnosis of doctors.

As a preferred embodiment, the bottom part 11 of the concentrator head 1 is preferred to be round, and the diameter is generally 1 cm to 3 cm. The distance from the highest point of the cavity 101 formed by the bottom part 11 to the lowest point of the resonant thin film 2 is 0.5 mm to 3 mm. The height of the concentrator part 12 is from 1 cm to 3 cm, and the inner diameter of the second cavity 102 formed is 3 mm to 6 mm. The arc formed by the hollow cavity 101 is a circular arc with a radius being 4 cm.

The said resonant thin film 2 is made of a plastic or PVC material to make the film have certain elasticity, easy to cause vibration through air, the resonant thin film 2 adopts a bottomless hollow cylinder shape, a limiting part 21 is arranged at the bottom extending outward, the width of the limiting part 21 is 1.5 mm to 5 mm, thereby meeting the limiting requirement to the largest extent and reducing the consumable materials. The thickness of the said resonant thin film 2 is 0.5 mm to 1 mm and its internal diameter is 4 cm to 8 cm.

The thin film fixed part 31 of the fixed element 3 is in a barrel shape without cover and bottom, and a limiting structure extending some certain distance inward is arranged at the end of the fixing part away from the resonant thin film 2, the width of the limiting structure is suitable for the limiting part 21 of the resonant thin film 2. This can limit the resonant thin film 2 to the thin film fixed part 31, so as to prevent falling off during normal use. At present, the existing technology has the problem that the whole fixed parts 3 and the thin film are manufactured in a whole, this makes it impossible to change, the whole needs to be changed if a part is damaged; this is not good for recycling, and this proposal allows to replace a fixed part 3 of different specifications according to the requirement.

A first internal thread is arranged at the inner side of the thin film fixed part 31, an anti-slide structure 36 is arranged at the outer side; vertical triangular column grooves are evenly arranged on the anti-slide structure 36, the triangular column is an equilateral triangle column, the side length of the equilateral triangle column is 0.8 mm to 1.3 mm, and all the corners are made round, so as to provide convenience for replacement of the think film fixed part 31, make it easy to disassemble, hold it up easily through the anti-slide structure 36 when installing other devices as required.

The joining part 32 comprises a ring edge 33 with a thickness of 1.2 mm to 1.8 mm and a base 34, wherein the base 34 is connected with and fixed on a sensor 4. A first external thread is arranged at the outer side of the ring edge 33 of the joining part in corresponding to the first internal thread at the inner side of the thin film fixed part 31, a connecting hole 35 is arranged at the center of the base 34 and connected to the sensor 4, a second internal thread is arranged in the connecting hole 35, to facilitate disassembly of the sensor 4, that is, a second external thread is arranged at the outer side of the sensor 4, and matches the second internal thread. The inner diameter length of the ring edge 33 is 2 cm to 4 cm longer than the diameter length of the connecting hole 35 of the base 34, and the outer side of the base 34 is frosted. This can ensure the whole device be better fixed and held, and can be used convenient with other devices. The existing diagnostic equipment can only be used alone, and is difficult to be used together with other diagnostic equipment; special personnel are required for maintenance or it is directly replaced, thereby increasing the burden of patients.

The sensor 4 comprises an air vibration sensor, a signal amplifier, an information converter and an external information interface. The external information interface is electrically connected with the information converter, and the air vibration sensor and the signal amplifier are electrically connected. The information converter converts the information obtained by the air vibration sensor into an electrical signal and transmits the information through the external information interface. The air vibration sensor captures the frequency of the vibration through air and amplifies the signal through a signal amplifier to further improve the murmur existing in the heart sound, to make it heard by a doctor or reflect the murmur more clearly in a monitoring waveform through an external signal monitoring processor.

The data transmission structure is an audio signal line, with one end being fixed on the external information interface of the sensor 4; or other signal transmission lines, such as type-c; this ensures the structure carries out data transmission with other monitoring equipment and cooperate with other equipment to better exert its adaptability and maximize its value.

A number of the above monitoring equipment can be used after being fixed by an external fixture, the equipment can be easily arranged at several points of a human heart position together, so as to facilitate real-time monitoring at multiple points at the same time, thereby realizing synchronous monitoring of the ECG and the heart sound and providing better feedback on the heart condition of the detected.

To sum up, this product has the advantages of simple structure design, convenient use, remarkable effect and good adaptability, and it can greatly help doctors to identify more potential problems of patients.

The prevent invention also includes some embodiments.

1. A device for detecting physiological sounds, the device comprising a thin film, and a first conductive element for conducting sounds, the conductive element being located on the thin film.

2. The detection device of clause 1, wherein the said film is an elastic film.

3. The detection device of clause 1 or claim 2, wherein the said detection device comprises a cavity, and the thin film is a part of the cavity.

4. The detection device of clause 13, wherein the volume of the cavity is variable.

5. The detection device of clause 3, wherein the said volume of the cavity is reduced, either when the conductive element contacts the skin of a human or a mammal, or before the conductive element contacts the skin of a human or a mammal, or after the conductive element contacts the skin of a human or a mammal.

6. The detection device of clause 3 to clause 5, wherein the said cavity is a sealed chamber, and the sealed chamber includes gas molecules.

7. The detection device of clause 3 to clause 6, wherein the density of the gas molecules in the cavity is increased, either when the conductive element contacts the skin of a human or a mammal, or before the conductive element contacts the skin of a human or a mammal, or after the conductive element contacts the skin of a human or a mammal.

8. The detection device of clause 3 to clause 7, wherein the said cavity is in sealed state, either when the conductive element contacts the skin of a human or a mammal, or before the conductive element contacts the skin of a human or a mammal, or after the conductive element contacts the skin of a human or a mammal.

9. The detection device of clause 1, wherein the said conductive element is located on the thin film, outside the cavity.

10. The detection device of clause 3, wherein the said cavity is communicated with the outside atmosphere before detecting the physiological sounds, and the said cavity is in sealed state when the conductive element contacts the skin.

11. The detection device of clause 10, wherein the cavity is communicated with the outside atmosphere through the conductive element, and the skin seals the conductive element to make the cavity in sealed state when the conductive element contacts the skin of a mammal or a human.

12. The detection device of clause 1, wherein the said sound conductive element is a metallic or nonmetallic element.

13. The detection device of clause 1, wherein the area that the conductive element contacts the surface of a mammal is smaller than the area of the thin film; or the projected area of the conductive element is smaller than the projected area of the thin film.

14. The detection device of clause 1, wherein the said metal is of conductive metal, such as iron, copper, aluminum, gold, silver, or any other metallic conductor or alloy.

15. The detection device of clause 1, wherein the density of the thin film is smaller than the density of the conductive element, or the weight per unit volume of the conductive element is smaller than the weight per unit volume of the thin film.

16. The detection device of clause 1 to claim 15, wherein the said thin film is a plastic film, preferred as PCV thin film.

17. The detection device of clause 6, wherein the said gas is a mixed gas molecule or a single gas molecule.

18. The detection device of clause 17, wherein the said gas is air.

19. The detection device of clause 3 to clause 6, wherein the pressure inside the cavity is increased, either when the conductive element contacts the skin of a human or a mammal, or before the conductive element contacts the skin of a human or a mammal, or after the conductive element contacts the skin of a human or a mammal.

20. The detection device of clause 3, wherein the said conductive element is a hollow element, one end of the element is closed and the other end is open, and the open end is communicated with the gas in the cavity.

21. The detection device of clause 3, wherein the cavity including the thin film is a second cavity, the conductive elements comprise the first cavity, and the first cavity is communicated with the second cavity for treating fluid.

22. The detection device of clause 21, wherein the first cavity and the second cavity forms a closed cavity.

23. The detection device of clause 3, wherein the conductive element includes openings at both ends, the opening at one end is communicated with the said cavity, and the opening at the other end is communicated to the outside atmosphere; in the territory of China, when the conductive element detects the physiological sounds, if the element contacts the skin of a mammal or a human, the opening at the other end is sealed by the skin so as to make the cavity in sealed state.

24. The detection device of clause 1, wherein the said device also comprises a second conductive element, the first conductive element being located on the thin film and the second conductive element winding around the first conductive element.

25. The detection device of clause 3, wherein the conductive element includes a closed end for contacting the skin of a mammal and an open end, the closed end being located in the second conductive element, and the open end communicated with the second cavity.

26. The detection device of clause 1, wherein, in some embodiments, the said thin film is either round, square or rhombic, and the sound conductive element is located at the center position of the thin film.

27. The device of clause 26, wherein the said film is round.

28. The detection device of clause 3, wherein the said device also comprises a sound sensor, and the sound sensor is used to sense the sound or vibration in the cavity.

29. The detection device of clause 3, wherein the said device also comprises a sound sensor; the sensor is located or partly located in the cavity and used to sense the vibration of the gas in the cavity.

The above are only the preferred embodiments of the invention, it should be noted that, the common persons skilled in the technical field, without departing from the idea of the invention, can also make some improvements and modifications, and these improvements and modifications should be considered as within the protection scope of the invention.

All patents and publications mentioned in the specification of the invention indicate that these are public technologies in the field, which can be used by the invention. All patents and publications quoted herein are also listed in the references, as each publication is specifically referenced separately. The invention described herein may be implemented in the absence of any one or more elements, one or more restrictions, which are not specially specified herein. For example, the terms "including", "comprising" and "consisting of" in each embodiment can be replaced by the other two. The so-called "one" herein only means "one", while excluding or only does not mean only including one, it can also mean including two or more. The terms and expressions used here are described without limitation, and it is not intended herein to indicate that the terms and interpretations described in this document exclude any equivalent feature, but it is understood that any appropriate alteration or modification may be made to the extent of the invention and claims. It can be understood that the embodiments described in the present invention are some preferred exemplary embodiments and features. Any person skilled in the art can make some variations and changes based on the essence described in the present invention. These variations and changes are also considered within the scope of the invention and the scope limited by the independent claims and the dependent claims.

The invention claimed is:

1. A device for detecting physiological sounds, the device comprising a thin film, and a conductive element for conducting sounds, the conductive element being located on the thin film, wherein the conductive element comprises a bottom part and a concentrator part, wherein the bottom part is polygonal or round, and peripheries of the bottom part gradually protrude from the thin film towards a center of the conductive element to form a first cavity with the thin film, and wherein the concentrator part is in a polygonal cylinder shape or a circular cylinder shape and is located at a highest point of the conductive element relative to the thin film;

wherein the conductive element has an open end and the open end is sealed with the thin film thus to form a first cavity in the conductive element, and the highest point of the concentrator part is 0.3 cm to 4 cm higher than the highest point of the thin film.

2. The detection device of claim 1, wherein the said film is an elastic film.

3. The detection device of claim 1, wherein the said detection device comprises a second cavity, and the thin film is a part of the second cavity.

4. The detection device of claim 3, wherein the volume of the second cavity is variable.

5. The detection device of claim 3, wherein the said volume of the second cavity is reduced after the conductive element contacts the skin of a human or a mammal.

6. The detection device of claim 3, wherein the said first and/or second cavity is a sealed chamber, and the sealed chamber includes gas molecules.

7. The detection device of claim 6, wherein the density of the gas molecules in the second cavity is increased after the conductive element contacts the skin of a human or a mammal.

8. The detection device of claim 6, wherein the said gas molecules are mixed gas molecules or a single gas molecule.

9. The detection device of claim 8, wherein the said gas molecules are air.

10. The detection device of claim 3, wherein the said first and/or second cavity is in sealed state, either when the conductive element contacts the skin of a human or a mammal, or before the conductive element contacts the skin of a human or a mammal, or after the conductive element contacts the skin of a human or a mammal.

11. The detection device of claim 3, wherein the said second cavity is communicated with the outside atmosphere before detecting the physiological sounds, and the said second cavity is in sealed state when the conductive element contacts the skin.

12. The detection device of claim 11, wherein the second cavity is communicated with the outside atmosphere through the conductive element, and the skin seals the conductive element to make the second cavity in sealed state when the conductive element contacts the skin of a mammal or a human.

13. The detection device of claim 3, wherein the pressure inside the second cavity is increased after the conductive element contacts the skin of a human or a mammal.

14. The detection device of claim 3, wherein the said conductive element is a hollow element, one end of the element is closed and the other end is open, and the open end is communicated with a gas in the second cavity.

15. The detection device of claim 1, wherein the said conductive element is located on the thin film, outside the second cavity.

16. The detection device of claim 1, wherein the said sound conductive element is a metallic or nonmetallic element.

17. The detection device of claim 1, wherein the area that the conductive element contacts the surface of a mammal is smaller than the area of the thin film; or the projected area of the conductive element is smaller than the projected area of the thin film.

18. The detection device of claim 1, wherein the conductive element is of conductive metal, and the conductive metal is iron, copper, aluminum, gold, silver, or any other metallic conductor or alloy.

19. The detection device of claim 1, wherein the density of the thin film is smaller than the density of the conductive element, or the weight per unit volume of the conductive element is smaller than the weight per unit volume of the thin film.

20. The detection device of claim 1, wherein the said thin film is a plastic film, and the plastic film is a PCV thin film.

* * * * *